United States Patent [19]
Yelvington

[11] Patent Number: 5,866,086
[45] Date of Patent: Feb. 2, 1999

[54] DEVICE FOR DESTRUCTION AND ENCAPSULATION OF SYRINGES

[75] Inventor: Richard Yelvington, Jacksonville, Fla.

[73] Assignee: Imagination Medical, Inc., Jacksonville, Fla.

[21] Appl. No.: 959,511

[22] Filed: Oct. 28, 1997

[51] Int. Cl.[6] .................................................. A61L 2/04
[52] U.S. Cl. .................. 422/308; 422/307; 422/255; 422/309; 422/287; 241/23; 241/606
[58] Field of Search .......................... 422/255, 285–287, 422/307–309; 241/606, 23, 99; 264/311, 503, 309–312

[56] References Cited

U.S. PATENT DOCUMENTS

| | | | |
|---|---|---|---|
| 5,207,994 | 5/1993 | Suzuki et al. | 422/307 |
| 5,213,758 | 5/1993 | Kawashima et al. | 422/307 |
| 5,320,804 | 6/1994 | Zakaria et al. | 422/307 |
| 5,401,444 | 3/1995 | Spinello | 422/307 |

*Primary Examiner*—Krisanne Thornton
*Assistant Examiner*—Fariborz Moazzam
*Attorney, Agent, or Firm*—Thomas C. Saitta

[57] ABSTRACT

A device for the sterilization and encapsulation of biohazardous materials, especially including needles and syringes, which provides a sealable container to receive the materials and a rotating carousel to successively position the container for processing, a heat device to raise the temperature within the container to sterilize the contents and melt any plastic material, a compactor to crush the container into a smaller volume, and an ejector to remove the compacted container from the carousel.

19 Claims, 4 Drawing Sheets

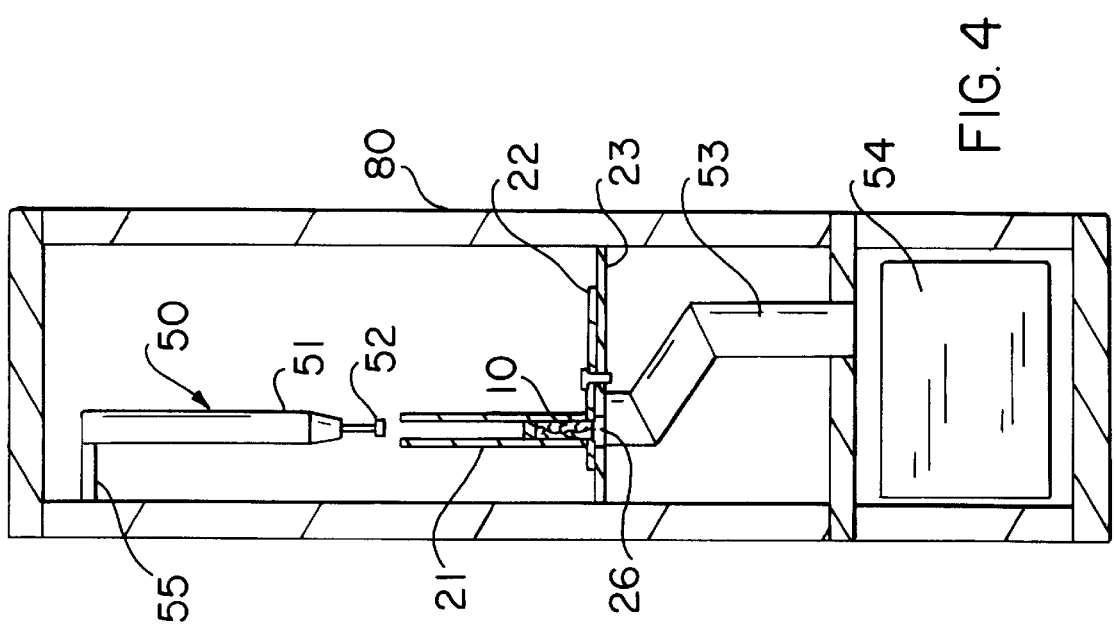

DEVICE FOR DESTRUCTION AND ENCAPSULATION OF SYRINGES

This application claims the benefit of U.S. Provisional application Ser. No. 60/029,514, filed Oct. 28, 1996.

BACKGROUND OF THE INVENTION

The invention relates generally to the field of devices which are used to safely destroy or encapsulate used syringes, needles or similar objects which may expose handlers to infectious diseases or similar biological hazards from accidental contact, sticks or punctures. In particular, the invention relates to such devices which sterilize the objects and melt any plastic present by exposing the objects to sufficiently high temperatures, which crush or compress the objects to present a compact waste product for disposal, and which encapsulate the non-meltable and sharp components to prevent punctures during subsequent handling. Even more particularly, this invention relates to such devices which provide a non-melting, crushable container to receive the object to be destroyed, where the container can be used for safe storage prior to destruction, and where the container itself is crushed to form the compact encapsulation means.

Syringes, needles and other similar objects are well-known in medical situations for use in delivering treatment fluids into the bloodstream or for removing blood samples. Syringes and needles are also used in a criminal manner to self-administer illegal drugs. There are numerous blood borne diseases, including HIV, TB, Hepatitis B & C, etc., which can be accidentally transferred from the carrier to another person coming into contact with the disease laden blood. Unfortunately, law enforcement and medical personnel must routinely deal with potentially contaminated syringes and needles and are thereby often exposed to such diseases during the handling, storage and disposal of the used syringes and needles. Law enforcement personnel often must retain and preserve the contaminated syringes and needles for use as evidence, presenting an increased likelihood that someone will be accidentally stuck.

Since the syringes and needles are considered bio-hazardous waste, special steps must be taken to properly and safely dispose of them. It is necessary both to sterilize any biological hazards present and to encase the sharp point of the needle to prevent accidental needle punctures. Once safely sterilized and encapsulated, the waste is non-hazardous and may be routinely disposed of in a non-regulated manner.

It is an object of this invention to provide a device which provides a means to safely and easily dispose of potentially hazardous syringes, needles or other bio-hazardous material by providing a non-meltable (at sterilization temperatures), crushable, sealable container sized to receive and store the syringe or needle in a manner which precludes accidental puncture during handling, and by further providing a means to sterilize, crush and encapsulate the syringe, needle or other hazardous material while retained within the sealable container. It is a further object to provide such a device where the sealable container is placed into the destruction means and sterilization, compaction and encapsulation are performed without need for further human contact. It is a further object to provide such a device where the plastic components of a syringe are melted to provide the primary encapsulation for the sharp needle and the sealed container acts as a secondary encapsulation for both the plastic and the needle.

SUMMARY OF THE INVENTION

The invention comprises in general a device for sterilizing, compacting and encapsulating bio-hazardous waste, such as a needle, syringe, contaminated soil sample, infectious culture or other bio-hazardous matter, which has the potential of transmitting infectious disease to handlers through accidental skin punctures. A needle, syringe or other hazardous material is placed into a sealable container made of a malleable material, such as for example aluminum, having a melting point well in excess of typical sterilization temperatures and which is sufficiently strong to preclude puncture of the container wall by the needle point during the compacting operation, the container being preferably configured in the shape of an elongated tube with one closed end and one end adapted to receive a removable cap or closure. The operational device comprises a port for placement of the container into a housing, means to heat the container to a temperature sufficient to melt any plastic components as well as to sterilize any bio-hazardous organisms or material present on the syringe or needle, means to compact the container, and means to deposit the compacted container into a collection receptacle.

The device uses a rotating carousel having at least one and preferably multiple open-ended receiver tubes into which a container is placed for treatment. The carousel translates, indexes and positions the container through successive treatment stages. In the first treatment stage, the container is heated by blowing high temperature air through the receiver tube, preferably at approximately 1200 degrees F. for approximately one minute with the air recycled for efficiency. The carousel is then rotated to the second stage, where a compactor, preferably a pneumatically or hydraulically operated piston, crushes the container within the receiver tube with approximately 250 pounds of pressure to a height of approximately one inch. The carousel is then rotated to the third position, where an ejector piston, which can be coupled in operation to the compactor piston, pushes the compacted container out the bottom of the receiver tube through an ejection port in the support base of the carousel and into a collection receptacle.

BRIEF DESCRIPTION OF THE DRAWINGS

FIG. 4 is a cross-sectional view taken along line IV—IV of FIG. 1 showing the ejection means.

DETAILED DESCRIPTION OF THE INVENTION

The device will now be described in detail with regard to the best mode and preferred embodiment, with direct reference to the various numbered drawings. In general, the invention is a device for the safe and efficient destruction, sterilization and encapsulation of bio-hazardous waste and other materials, and in particular for such waste as needles, syringes and other objects which present the potential for puncturing or cutting the skin of persons handling the objects. The invention provides for the storage of the hazardous objects in a resealable container formed of a malleable metal suitably puncture-resistant to needles at pressures required to crush the container, where the device receives the container, heats the container to a temperature sufficient to sterilize any infectious hazards and, in the case of a syringe, to melt the plastic to surround and retain the point of the needle in a hard plastic puck when the plastic cools, and finally compacts the container into a smaller configuration. Preferably, the device also provides means to eject the compacted container into a waste receptacle without need for direct handling. Also preferably, the device provides means to transport the container internally to various stations or positions within the housing of the device, such that the steps of heating, compacting and ejecting occur at different stations.

Figure 5:
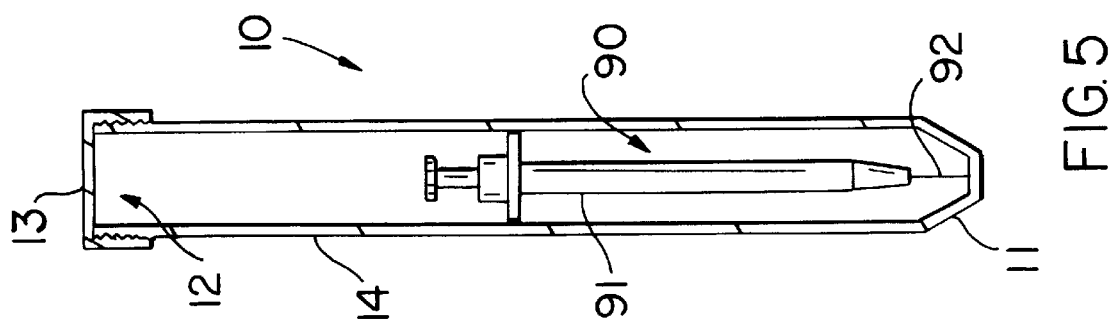
FIG. 5 is a cross-sectional view of a sealed container containing a syringe.

Referring now to FIG. 5, the container 10 for the hazardous material 90 is seen to be a generally elongated hollow tube with a closed end 11, side wall 14, an open end 12 and a closure member or cap 13. The shape and size of the container 10 is preferably sufficient to receive and retain a syringe 91 with a needle 92, although other configurations are contemplated within the scope of the invention. The container 10 is formed of a deformable or malleable material which will maintain its integrity when crushed, which is essentially puncture-proof to needles 92, and which does not melt at temperatures sufficient to sterilize objects contained within, and is preferably formed of a metal such as aluminum. Preferably, the closure member 13 is removable such that the container 10 can be sealed and resealed, allowing the hazardous material 90 to be removed and replaced if required. In the preferred embodiment shown, the open end 12 and closure member 13 are threaded to allow the container 10 to be sealed and opened by axial rotation of the closure member 13, but it is understood that other equivalent means to close the container 10, such as a mechanical interlock or force-fit construction, could also be utilized. Preferably, the closed end 11 of the container 10 is rounded so that no edges or corners are present and is formed slightly thicker than the side wall 14. The relatively thin side wall 14 allows the container 10 to be crushed at a relatively low compaction pressure, while the thicker closed end 11 insures that a needle 92 will not puncture the closed end 11 and will be retained within the container 10 when compacted. For example, a container suitable for this contemplated use constructed out of aluminum and sized to receive a syringe 91 and needle 92 may have a length of approximately 7.25 inches, an outer diameter of approximately 0.86 inches, a side wall 14 thickness of approximately 0.007 inches and a closed end 11 thickness of approximately 0.02 inches. The closure member 13 is also preferably of increased thickness relative to the side wall 14 since the force of compaction will be directed against the closure member 13.

Figure 6:
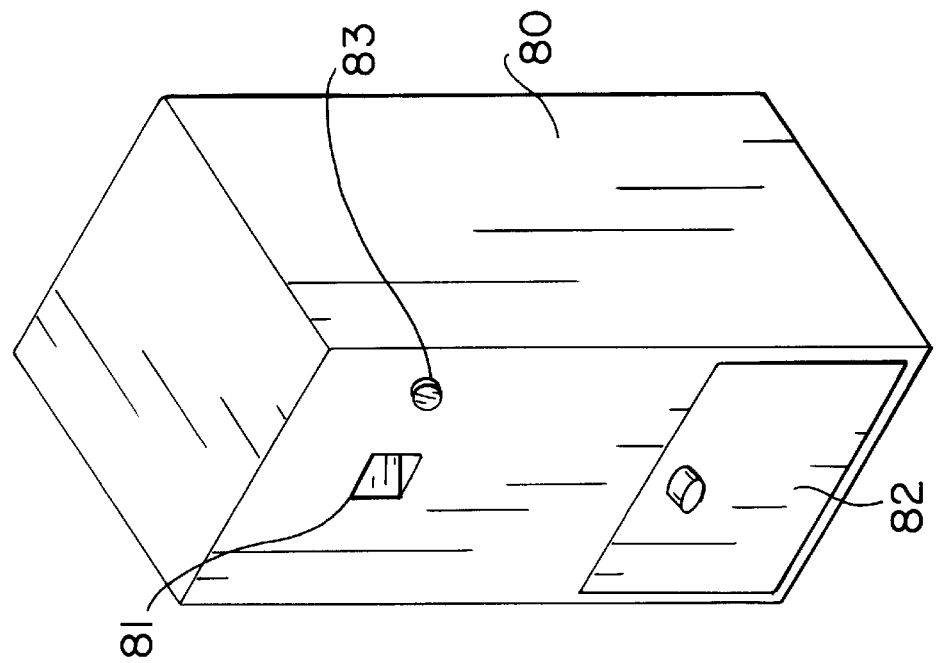
FIG. 6 is a plan view of the housing.

As seen in FIG. 6, the device comprises in general a housing 80, shown as generally rectangular but other configurations are also possible, which fully encloses the operational elements of the device. Container receiving means 81, such as a load chute, is provided on the top or side of the housing 80 to receive the container 10 to be destroyed, and preferably comprises an aperture only slightly larger in diameter than the diameter of the container 10 to preclude insertion of improper objects and as a safety feature. A door or other closure means may be provided over the load chute 81. An access door 82 provides means to access the compacted containers 10 for removal and ultimate disposal. An activation switch 83 is externally mounted to initiate processing of the container 10, or in the alternative automatic activation means, such as a photo-electric, pressure or contact switch, not shown but well known in the art, may be incorporated such that the processing steps begin automatically whenever a container 10 is loaded into the load chute 81. Preferably, progression from one processing stage to the next is also automatic, controlled by a microprocessor controller or other timer means known in the art.

Figure 1:
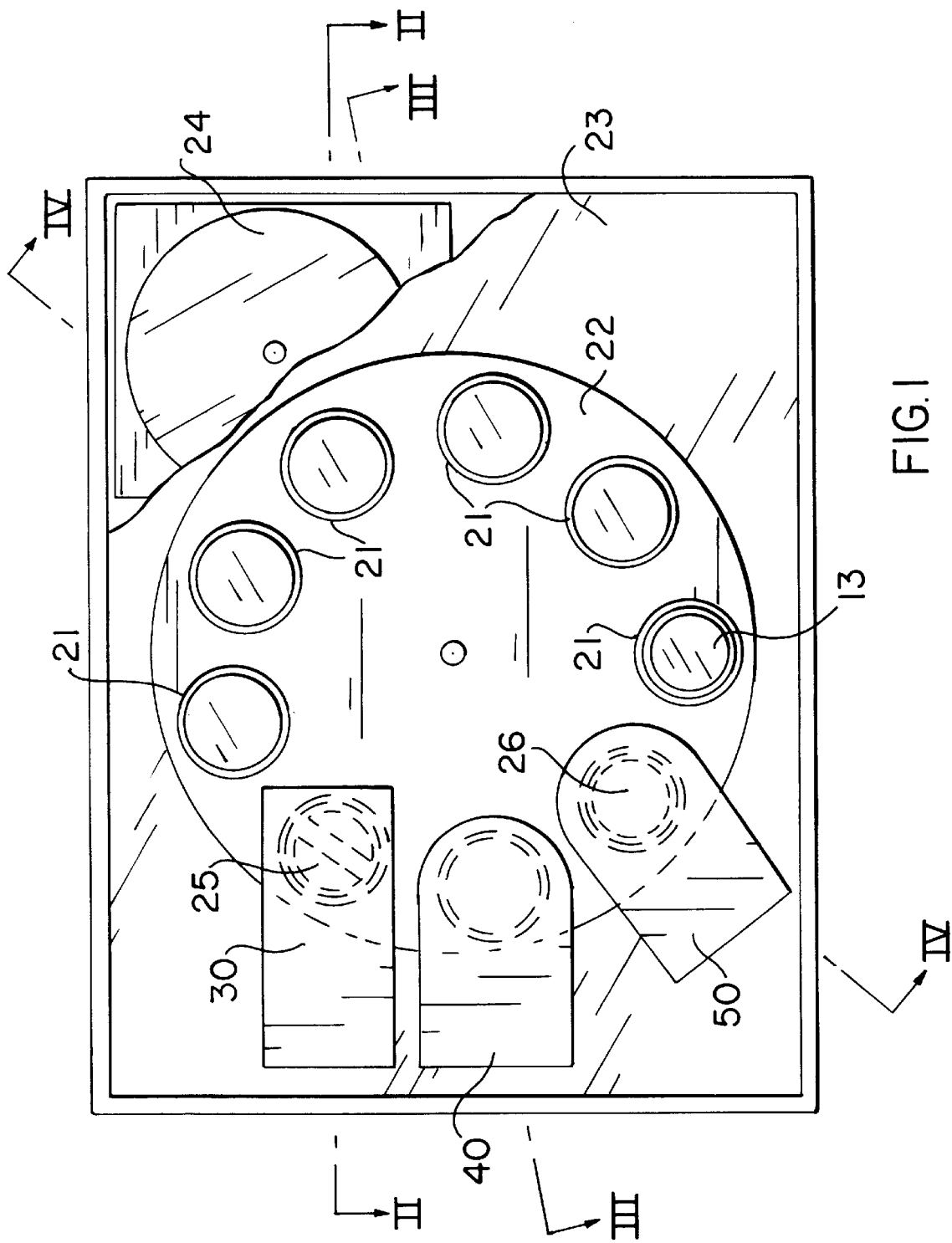
FIG. 1 is an exposed vertical view showing the transport carousel.

The load chute 81 directs the container 10 into a generally vertically oriented receiving tube 21 which is a component of transport means 20. Transport or indexing means 20 comprises a mechanical system which relocates or indexes the container 10 to various stages or positions for processing, and may comprise any of a number of known mechanical systems suitable for moving the container 10 within the housing 80. Preferably, as shown in FIG. 1, the transport means 20 comprises a rotating turntable or carousel 22 mounted directly above a stationary retainer plate 23, the carousel 22 having at least one and preferably plural receiving tubes 21 mounted thereon, the receiving tubes 21 being open at both ends and having a length greater than the length of the container 10 and a diameter slightly larger than the outer diameter of the container 10. By providing plural receiving tubes 21, multiple containers 10 can be loaded into the device and processed at the same time. The carousel 22 is correspondingly apertured beneath each receiving tube 21 such that a container 10 will freely pass through said carousel 22 except where prevented by retainer plate 23. The carousel 22 is rotated by suitable drive motor means 24 which both rotates and indexes the carousel 22 to each successive processing position. Drive motor means 24 may rotate and index the carousel 22 by direct contact, gearing, belt drive, chain drive, or any other suitable mechanism well known in the art. FIG. 1 shows a carousel 22 with nine receiving tubes 21 and the heating means 30, compactor means 40 and ejector means 50 positioned adjacently. A simpler version of the device could also be constructed, among other possible variations, with the load chute 81, heating means 30, compactor means 40 and ejector means 50 located symmetrically at 90 degree intervals relative to the axis of carousel 22 and four receiving tubes 21 also mounted on carousel 22 symmetrically at 90 degree intervals, in which case processing would begin with one rotational indexing movement. Even more simply, the device could utilize a single receiving tube 21 which is successively rotated through the stations.

Figure 2:
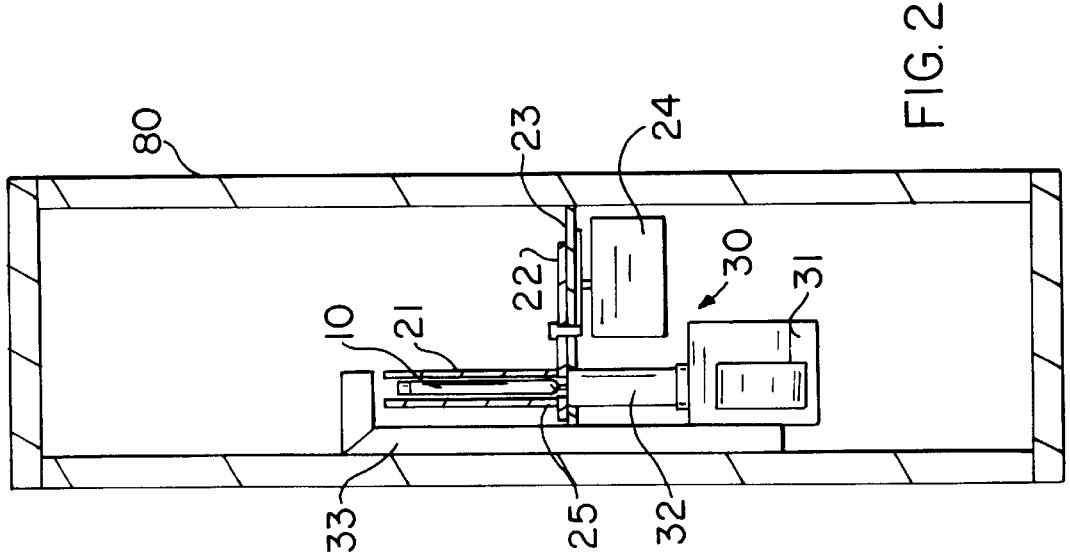
FIG. 2 is a cross-sectional view taken along line II—II of FIG. 1 showing the heating means.

A container 10 loaded into load chute 81 falls into one of the receiving tubes 21 occupying the load or receiving station location, is retained therein by the stationary retainer plate 23 directly below the carousel 22, and is indexed by drive motor means 24 into the first processing position or station, as shown in FIG. 2. The first station is for sterilization of the bio-hazardous waste 90 and secondarily for melting any plastic present in the container 10. The container 10 is positioned such that it is exposed to means 30 to elevate the temperature within the container 10 to a temperature sufficient to sterilize the hazardous matter 90, preferably at least approximately 1200 degrees F., although this temperature may vary depending on the particular hazardous material 90 being processed. Heating means 30 may comprise any known apparatus for suitably raising the temperature within the tube, such as for example electrical resistance heating, but preferably is a forced hot air apparatus comprising a hot air blower or heat gun 31 which blows or forces air past a series of resistance coils, a hot air supply chute 32 which directs the hot air into the receiving tube 21 located in the first stage position and around the container 10. Preferably, a recycling conduit 33 traps the hot air exiting the receiving tube 21 and routes it back through the blower 31. The retainer plate 23 is provided with a sterilization aperture 25 at the first processing stage to allow the hot air to pass through it while retaining the container 10 in the carousel. The sterilization aperture 25 may be slotted or provided with small openings to create a grid or mesh pattern. The container 10 is maintained at this station sufficient time to insure that the temperature within the closed container 10 is sufficiently elevated, after which the heating means 30 deactivates and the carousel 22 is rotated by drive means 24 to position the container 10 at the second processing station for compaction. Where the hazardous material 90 comprises a plastic syringe 91 with metal needle 92, the heat of sterilization will also serve to melt the plastic material, resulting in a metal needle 92 situated at the bottom of the container 10 and surrounded by molten plastic. When the plastic cools, it will harden into an encapsulating plastic puck to safely encase the sharp point of the needle 92.

Figure 3:
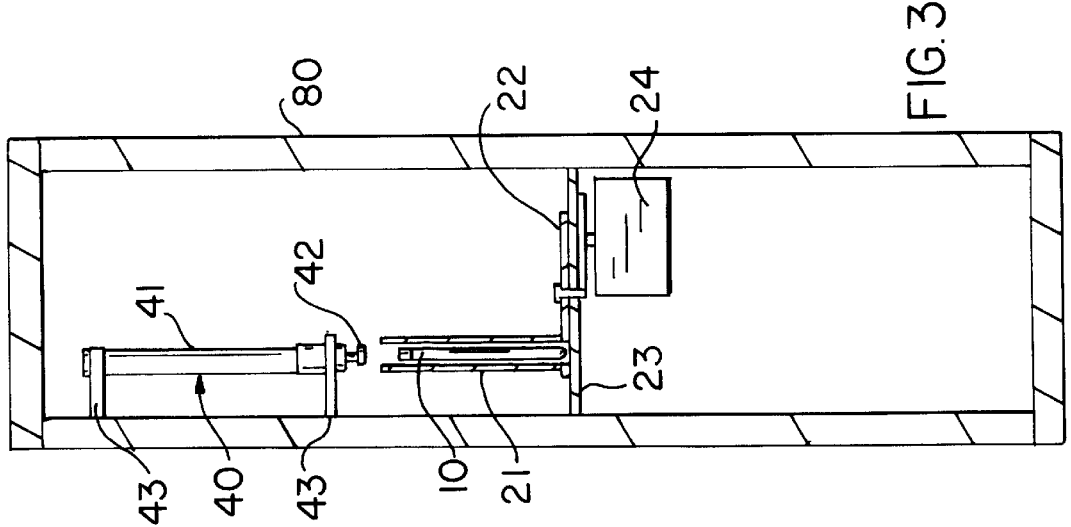
FIG. 3 is a cross-sectional view taken along line III—III of FIG. 1 showing the compaction means and the carousel drive means.

As seen in FIG. 3, at the second processing station the container 10 and receiving tube 21 are positioned coaxially with the hydraulic piston 41 of compactor means 40, which is mounted onto the housing 80 by suitable brackets 43. Hydraulic piston 41 has a compactor head 42 having a diameter just slightly smaller than the interior diameter of the receiving tube 21. The hydraulic piston 41 is sized to deliver sufficient force to crush the container 10 to a much smaller volume, and typically needs to deliver approximately 250 pounds of pressure for an aluminum container 10 as described previously. When the container 10 is positioned beneath the hydraulic piston 41, the compactor head 42 is advanced into the receiving tube 21 until it contacts and compacts the container 10 to a height of approximately one inch, thereby significantly reducing the total volume of the container 10 and precluding any accidental or purposeful removal of the hazardous matter 90. The retainer plate 23 is solid, and possibly even reinforced, beneath the container 10 at this location such that the container 10 is compacted into a relatively solid slug. Where the hazardous waste 90 comprises a syringe 91 and needle 92, the melted and then hardened plastic will provide a first means of encapsulation for the point of the needle 92 and the compacted container 10 will provide the second means of encapsulation. After the compactor head 42 is withdrawn from the receiving tube 21, the compacted container 10 is advanced to the third and final processing station.

As shown in FIG. 4, the third processing station aligns the receiving tube 21 containing the compacted container 10 with an ejection aperture 26 in retainer plate 23, which is sized equal to or preferably slightly larger than the interior diameter of receiving tube 21. At this stage, ejector means 50 is used to displace the compacted container 10 from the receiving tube 21 and carousel 22. Ejector means 50 comprises any suitable mechanism to eject the container 10, and preferably comprises an ejector piston 51 mounted onto the housing 80 by brackets 55 and having an ejector head 52 sized to fit within the receiving tube 21, such that when the ejector head 52 is advanced into the receiving tube 21, it forces the compacted container 10 out through the ejection aperture 26 in the retainer plate 23. A directional disposal chute 53 may be located beneath the ejection aperture 26 to receive and direct the container 10 into a waste area or receptacle 54 for later removal through access means 82, such as a door. The ejector piston 51 may comprise a pneumatic or hydraulic piston which operates independently of the compactor means 40, or it may be directly linked to the hydraulic compactor piston 41 such that operation of the compactor means 40 also operates the ejector piston 51, meaning that a single power or drive means may be used for both pistons 41 and 51. Once the container 10 is ejected from the receiving tube 21, the carousel 22 is indexed back into the original starting position for receipt of another container 10 to be processed.

It is understood that equivalents and substitutions to certain components or elements et forth above may be obvious to those skilled in the art, and thus the true scope and definition of the invention therefore is to be as set forth in the following claims.

I claim:

1. A device for the destruction, sterilization and encapsulation of hazardous material composed at least partially of meltable plastic and a non-meltable metal needle, said device comprising a sealable, deformable, elongated, metal container to receive said hazardous material, a housing to receive said container in a sealed state, means within said housing to heat said container to elevate the temperature within said container to a temperature sufficient to melt said plastic so as to encapsulate said needle and means within said housing to compact said container into a smaller volume such that said hazardous material remains encased within said container.

2. The device of claim 1, further comprising transport means to transfer said container from a first station within said housing where said heating means elevates the temperature within said container to a second station within said housing where said compactor means compacts said container.

3. The device of claim 2, further comprising ejector means within said housing to eject said container from said transport means.

4. The device of claim 2, where said transport means comprises a rotating carousel having at least one receiving tube to receive said container, where said rotating carousel relocates said receiving tube from said first station to said second station, and where said container comprises an elongated hollow tube having a closed end, an open end and a closure member which seals said open end.

5. The device of claim 4, where said rotating carousel is positioned above a retainer plate within said housing, said retainer plate having a sterilization aperture at said first station.

6. The device of claim 4, further comprising a third station within said housing and ejection means at said third station to eject said container from said transport means.

7. The device of claim 6, where said rotating carousel is positioned above a retainer plate within said housing, said retainer plate having an ejection aperture at said third station, said ejection aperture being of sufficient size to allow passage of said container therethrough.

8. The device of claim 6, where said ejection means comprises a piston having an ejection head which fits within said receiving tube.

9. The device of claim 8, where said compactor means comprises a piston having a compaction head which fits within said receiving tube.

10. The device of claim 4, where said heating means forces hot air past said container.

11. A device for the destruction, sterilization and encapsulation of hazardous material composed at least partially of meltable plastic and a non-meltable metal needle, said device comprising in combination:

(A) a housing having means to receive a sealed container containing hazardous material;

(B) a sealable container made of a deformable metal to receive and retain hazardous material composed at least partially of meltable plastic and a non-meltable metal needle;

(C) heating means within said housing to heat said container to a temperature suitable for sterilizing said hazardous material and melting said plastic in said hazardous material so as to encapsulate said needle;

(D) compactor means within said housing to compact said container into a smaller total volume;

(E) access means to remove said container from said housing after it has been compacted.

12. The device of claim 11, where said heating means is located at a first station within said housing and said compactor means is located at a second station within said housing, and further comprising:

(F) transport means to move said container from said first station to said second station.

13. The device of claim 12, where said transport means comprises a rotating carousel having at least one receiving tube to receive said container, said receiving tube being open on either end and said carousel being mounted directly above a retainer plate within said housing, said retainer plate retaining said container within said receiving tube.

14. The device of claim 13, further comprising:

(G) ejector means located at a third station within said housing to eject said container from said receiving tube after said container has been compacted by said compactor means, said retainer plate having an ejection aperture at said third station of sufficient size to allow passage of said container through said retainer plate.

15. The device of claim 14, where said compactor means comprises a piston having a compaction head sized to fit within said receiving tube and where said ejector means comprises a piston having an ejection head sized to fit within said receiving tube.

16. The device of claim 15, where said heating means comprises a hot air blower.

17. The device of claim 16, where said retainer plate has a sterilization aperture located at said first stage.

18. The device of claim 17, where said container comprises an elongated hollow tube having a closed end, a wall, an open end, and a closure member to seal said open end.

19. The device of claim 18, where said closed end is thicker than said wall.

* * * * *